United States Patent [19]

Friedman

[11] Patent Number: 4,589,411
[45] Date of Patent: May 20, 1986

[54] ELECTROSURGICAL SPARK-GAP CUTTING BLADE

[76] Inventor: Aaron Friedman, 45 Stonegate Dr., Wethersfield, Conn. 06109

[21] Appl. No.: 699,664

[22] Filed: Feb. 8, 1985

[51] Int. Cl.⁴ ............................................. A61B 17/36
[52] U.S. Cl. .......................... 128/303.14; 128/303.17; 331/127
[58] Field of Search ...................... 128/303.14, 303.17, 128/422, 800, 804; 313/131 R, 131 A, 140, 309, 352; 331/127

[56] References Cited
PUBLICATIONS

*Health Devices* Sourcebook, 1981–1982 Reference p. 283 et seq.
*Plastics Design Forum,* Jan./Feb. 1985.

*Primary Examiner*—Kyle L. Howell
*Assistant Examiner*—Randy Citrin
*Attorney, Agent, or Firm*—Hoffmann, Dilworth, Barrese & Baron

[57] ABSTRACT

A spark-gap cutting blade for an electrosurgical active electrode pencil which has a central electrode surrounded by an insulator and a series of alternating electrically conductive and insulative elements. The central electrode is electrically connected to one side of a high voltage source and the last electrically conductive element in the series is connected to the other side.

13 Claims, 5 Drawing Figures

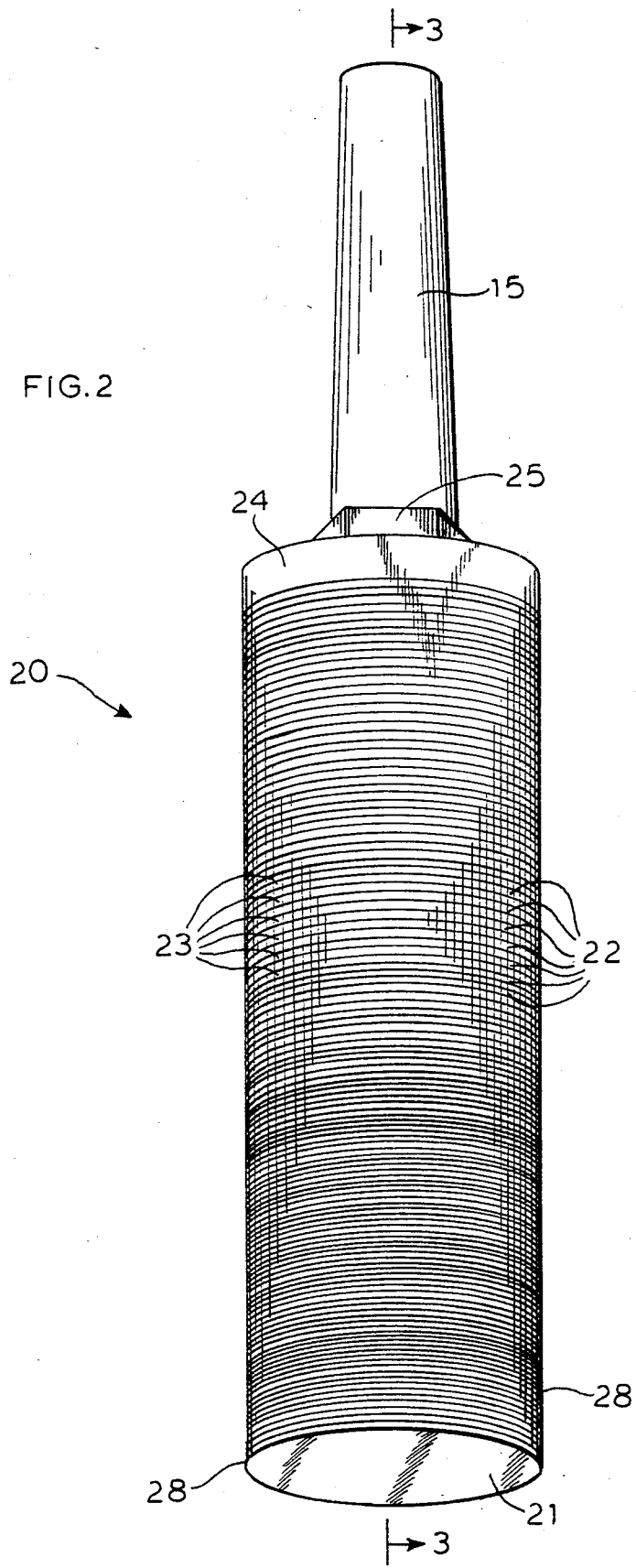

ELECTROSURGICAL SPARK-GAP CUTTING BLADE

BACKGROUND OF THE INVENTION

This invention belongs to the field of surgical cutting instruments and, in particular, to an electrosurgical active electrode pencil.

In electrosurgery, a high voltage current, for example, one of about 1,500 volts, is introduced through a cable to a hand-held active electrode pencil equipped with a relatively long, thin metal blade which serves to focus the current in the area of the patient being operated upon. Operating in either the "cut" mode to cut through tissue or the "coag" mode to coagulate or cauterize capillaries which have been cut during the surgical procedure, the surgeon places the metal blade of the pencil in contact with the particular tissue site to be affected. Electrical current jumping from the blade to the tissue performs the cutting or coagulating operation as desired. To complete the circuit, the current passes through the affected site along the line of least resistance to an electrically conductive plate, commonly one fabricated of stainless steel, which supports the patient during the surgery.

Electrosurgery has been widely used to carry out surgical operations which are not readily or conveniently performed with mechanical cutting instruments or where bleeding is difficult to control. However, the known type of electrosurgical devices employing the aforementioned electrically conductive plate are subject to a number of disadvantages. Thus, a significant number of patients experience painful burns resulting from arcing currents between the patients' bodies and the underlying plate in areas of poor contact between the two. The known types of devices can interfere with the proper functioning of electronic implants such as pacemakers and have even been known to cause arcing within metallic prosthetic implants such as metal joints resulting in welding of the articulated parts.

SUMMARY OF THE INVENTION

It is an object of the present invention to provide an electrosurgical cutting instrument which does not require the use of a metal plate to complete the circuit.

It is a further object of the invention to provide a spark-gap cutting blade for an electrosurgical active electrode pencil which can assume a variety of configurations for particular applications.

In keeping with the foregoing objects, there is provided a spark-gap cutting blade for an electrosurgical active electrode pencil which comprises:
   (a) a central electrode terminating in an exposed first electrically conductive element;
   (b) an insulator surrounding the central electrode except the first electrically conductive element;
   (c) a series of electrically insulative elements alternating with electrically conductive elements disposed upon the insulator surrounding the central electrode, said series of insulative and conductive elements forming, together with the first electrically conductive element, a spark-gap cutting surface;
   (d) an electrical connector connecting the central electrode to one side of a high voltage source; and;
   (e) an electrical connector connecting the last electrically conductive element in the series of alternating insulative and conductive elements to the other side of a high voltage source.

By dispensing with the electrically conductive plate associated with prior electrosurgical devices, the electrosurgical active electrode pencil of this invention with its spark-gap cutting blade overcomes the disadvantages attendant the former as discussed above.

BRIEF DESCRIPTION OF THE DRAWINGS

FIG. 2 is a greatly enlarged perspective view of the spark-gap cutting blade of FIG. 1.

DESCRIPTION OF THE PREFERRED EMBODIMENTS

Figure 1:
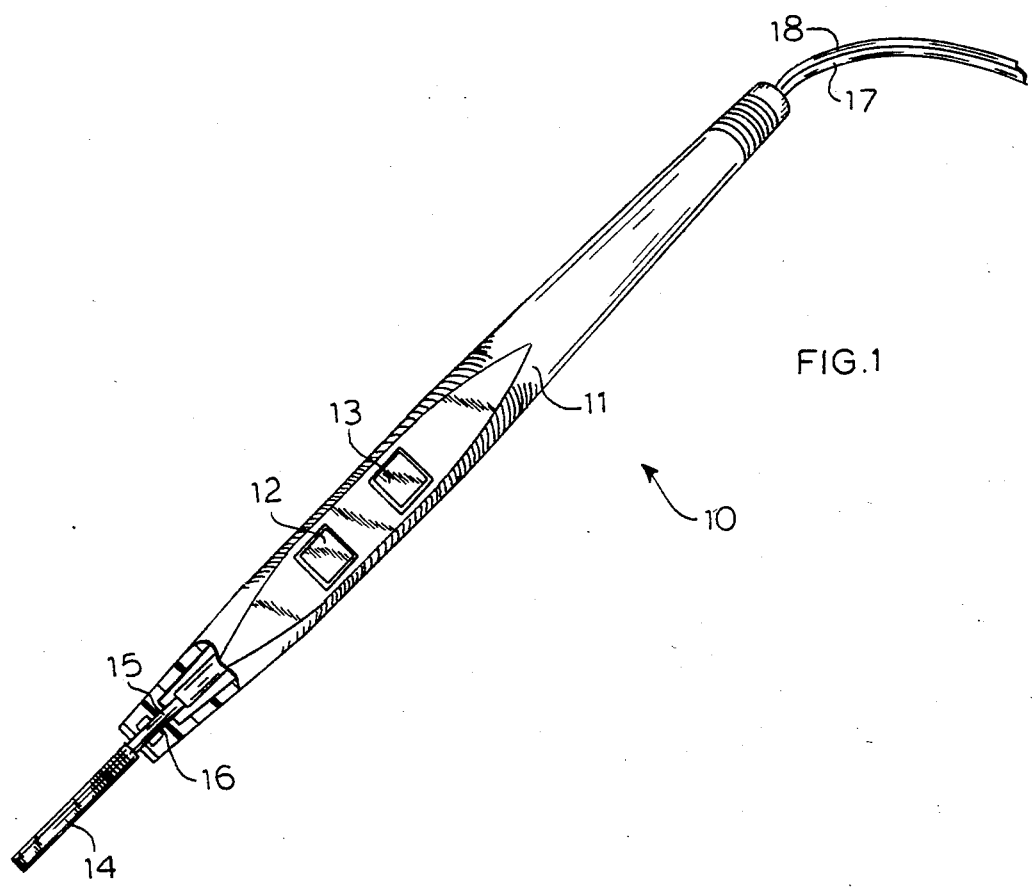
FIG. 1 is a perspective view of an electrosurgical active electrode pencil showing a portion of the pencil enclosure cut away where the spark-gap cutting blade is inserted.

In accordance with FIG. 1, an electrosurgical active electrode pencil is shown generally at 10 with the pencil enclosure at 11. Buttons 12 and 13 activate switches which operate the device in a cut mode and a coagulating mode, respectively. Spark-gap cutting blade 14 is inserted by its shaft 15 into channel 16 where the various electrical connections are made. Cable 18 is connected to one side of a high voltage electrical source and cable 17 is connected to the other side of said source to complete the circuit.

In the greatly enlarged view of spark-gap cutting blade 20 shown in FIG. 2, shaft or core 15 of the electrically insulated central electrode terminates in a first electrically conductive element 21 which may be affixed to the electrode or integrally formed therewith. Both the electrode and its exposed conductive element can be fabricated of the same material, e.g., nichrome or stainless steel. A series of alternating electrically conductive elements 22 alternate with like-configured electrically insulative elements 23. This series of elements is disposed about the core of the central electrode but prevented from direct contact therewith by an insulating sheath 30 as shown in FIG. 3. The edges 28 of each element in the series taken together make up the cutting edge of the blade. The first element of the series is an insulating disc, for example, of polyamide resin or other electrically insulative material, and the last element in the series is a somewhat thicker conducting disc 24. The conducting elements are preferably made of the same material as the electrode and first electrically conductive element. The entire series of alternating insulating and conducting elements is held in place by a nut 25 or equivalent fastening means. In operation, current flowing through the central electrode forms an arc at electrically conductive element 21 which continuously sequentially jumps to each of the electrically conductive elements 22 to form a spark-gap cutting edge along the entire length of the series of conductive and insulative elements forming the blade.

Figure 2A:
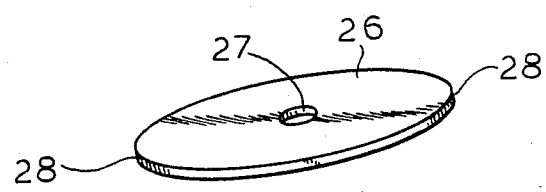
FIG. 2a is a perspective view of a single electrically conductive element of the cutting blade of FIG. 2.
Figure 3:
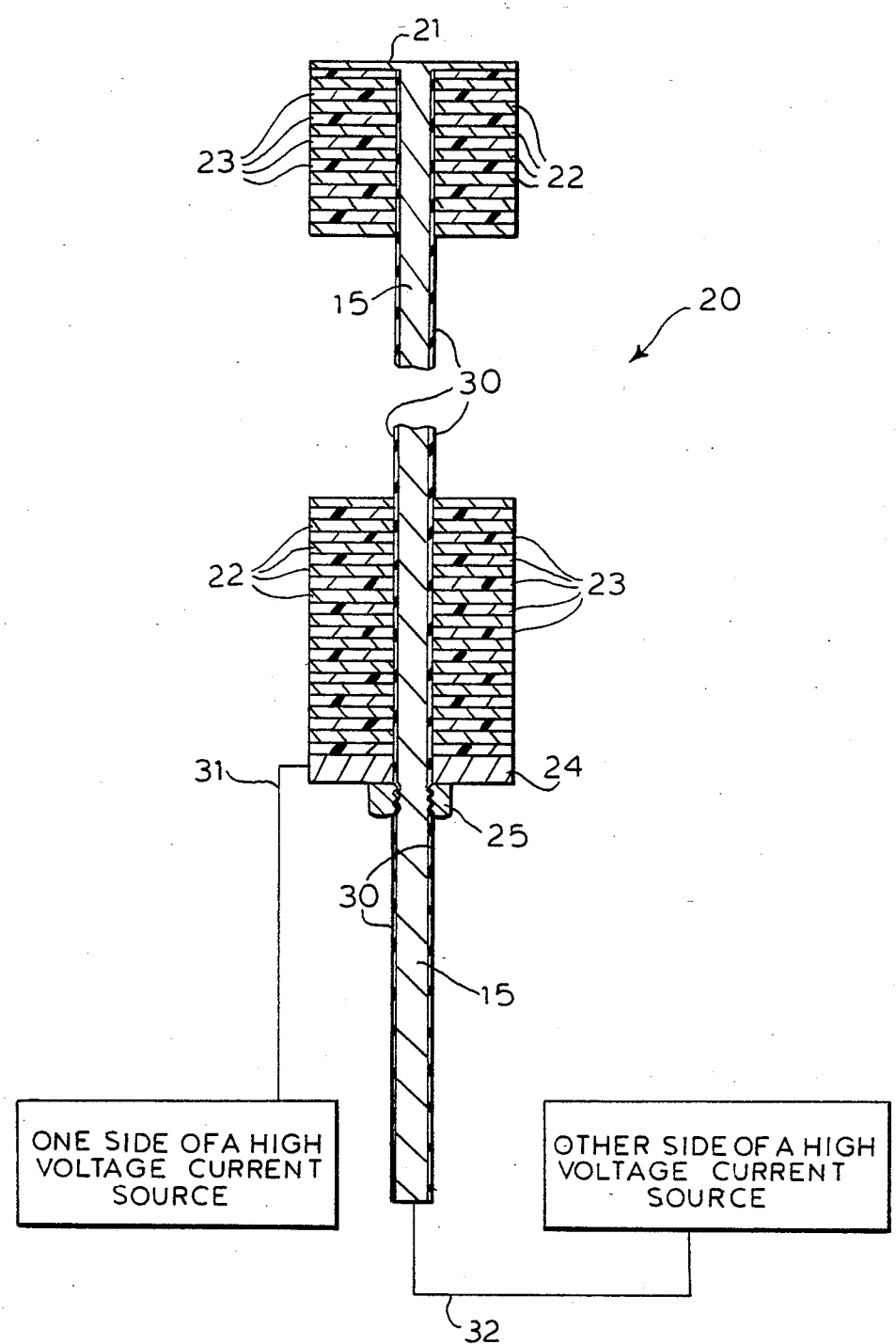
FIG. 3 is a sectional view of the cutting blade of FIG. 2a taken along line 3—3.

As shown in FIG. 2a, a typical individual electrically conductive element 26 possesses a centrally positioned orifice 27 whose configuration corresponds to the configuration of the insulated core of the central electrode. The thickness 28 of the element can vary up to the maximum arcing distance of the spark generated along the length of the cutting blade when the device is in use. In general, thicknesses of from 0.002 to 0.003 inches are entirely suitable. The insulating elements are essentially identical with the electrically conductive elements and may possess the same thickness. A variety of shapes are possible in addition to the elliptical one shown. Thus, the electrically conductive and insulating elements can be round, concave or convex in cross section. It is preferred that orifice 27 be other than circular in shape so that when fitted to the core of the insulated central electrode, the element will not rotate thereon but will remain in place.

In the sectional view of the cutting blade 20 shown in FIG. 3, the shaft or core 15 of the central electrode terminates in a first electrically conductive element 21. An insulator 30, for example, of a polytetrafluoroethylene resin, is fitted to the core 15 of the central electrode and can be shrunk-wrapped thereon to provide a snug fit with the core. Insulator 30 prevents electrical contact of alternating electrically conductive elements 22 with the shaft of the central electrode. The series of elements 22 and 23 are held in place by a nut 25. Wire 31 provides electrical contact between the last, relatively thick electrically conductive element 24 and one side of a high voltage current source and wire 32 provides electrical contact between core 15 of the central electrode and the other side of the high voltage current source. Wire 31 can be connected to the positive side of the voltage source and wire 32 to the negative side of the voltage source and vice versa. The voltage source can be either a direct current or an alternating current source.

Figure 4:
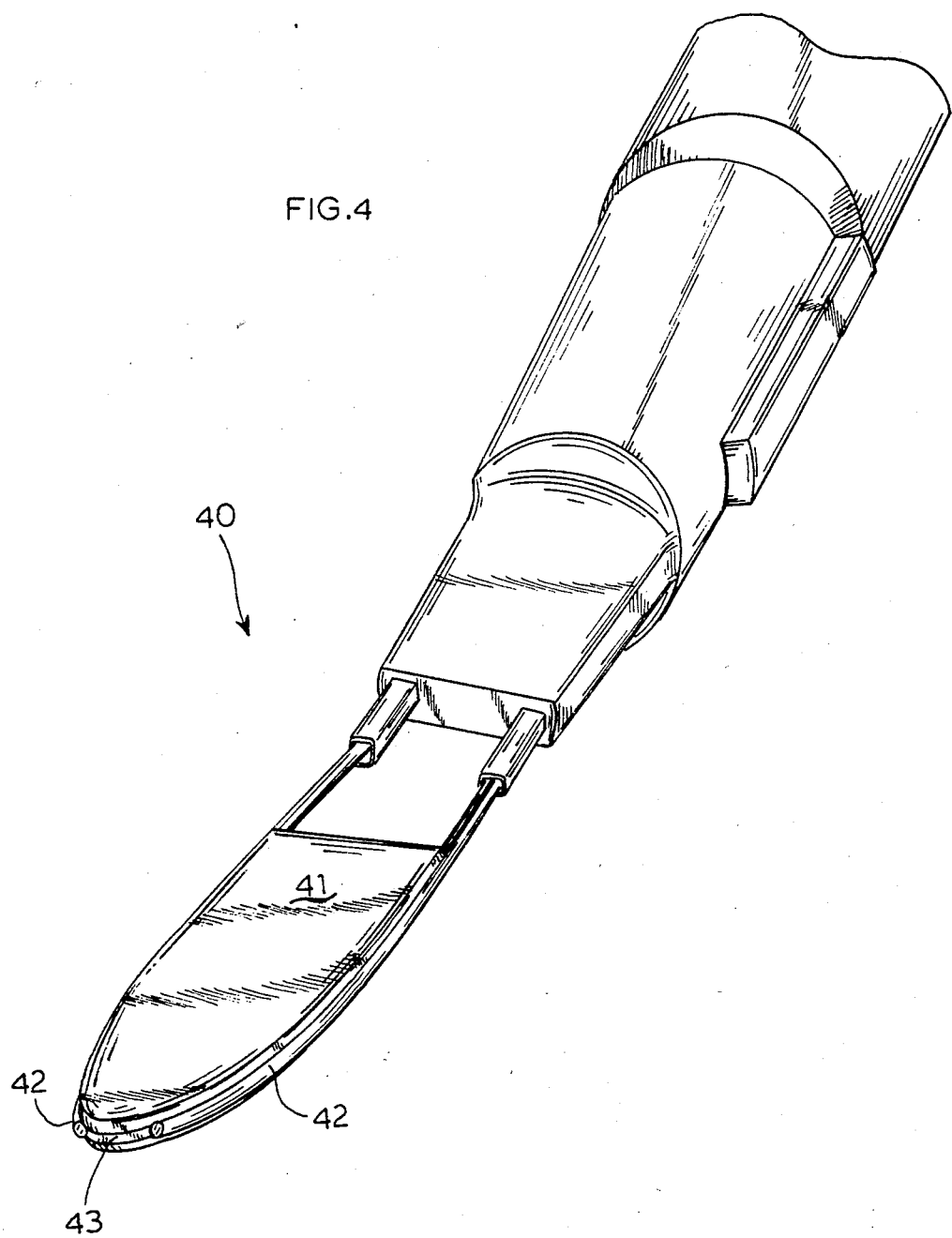
FIG. 4 is an enlarged perspective view of the improved heating element of an ophthalmic cauterizing device.

FIG. 4 illustrates an improvement in another type of electrosurgical device in accordance with this invention. In a known type of ophthalmic cauterizing device having a thin (e.g., 0.002" diameter) electrically powered free-standing loop heating element, due to the thinness of the heating element, it is easily mechanically distorted unless held to a relatively modest size, for example, one-half inch length or less measured from the base of the loop to its tip. In the improved ophthalmic cauterizing device 40 of FIG 4, thin loop heating element 42 is maintained in a substantially non-flexing condition by being supported within the groove 43 of a thermally stable (up to 1000° C. or more) non-conductive support element 41 which can be affixed to the loop heating element through a solder or other thermally stable adhesive or can be held in place through the tension of the loop itself. The support element can be fabricated from ceramic or other temperature resistant non-conductive material including some kinds of synthetic resin. Supported in the manner shown, the thin wire heating element 42 can be made to extend much further and/or to assume more varied configurations than is possible with the heating elements of known ophthalmic cauterizing devices.

Obviously, other modifications and variations of the present invention are possible in the light of the above teachings. It is, therefore, to be understood that changes may be made in the particular embodiments of this invention which are within the full intended scope of the invention as defined by the appended claims.

What is claimed is:

1. A spark-gap cutting blade for an electrosurgical active electrode pencil which comprises:
    (a) a central electrode terminating in an exposed first electrically conductive element;
    (b) an insulator surrounding the central electrode except the first electrically conductive element;
    (c) a series of electrically insulative elements alternating with electrically conductive elements disposed upon the insulator surrounding the central electrode, said series of insulative and conductive elements forming, together with the first electrically conductive element, a spark-gap cutting surface;
    (d) an electrical connector connecting the central electrode to one side of a high voltage source; and;
    (e) an electrical connector connecting the last electrically conductive element in the series of alternating insulative and conductive elements to the other side of a high voltage source.

2. The spark-gap cutting blade of claim 1 wherein the central electrode, the first electrically conductive element and the remaining electrically conductive elements are fabricated of stainless steel.

3. The spark-gap cutting blade of claim 1 wherein the central electrode, the first electrically conductive element and the remaining electrically conductive elements are fabricated of nichrome.

4. The spark-gap cutting blade of claim 1 wherein the electrically insulative elements are fabricated from a polyamide.

5. The spark-gap cutting blade of claim 1 wherein the insulator surrounding the central electrode is fabricated from a polytetrafluoroethylene resin.

6. The spark-gap cutting blade of claim 1 wherein the electrically insulative elements possess a thickness of from 0.002 to 0.003 inches.

7. The spark-gap cutting blade of claim 1 wherein the electrically conductive elements possess a thickness of from 0.002 to 0.003 inches.

8. The spark-gap cutting blade of claim 1 wherein the central electrode is connected to the positive side of a high voltage power source and the last electrically conductive element in the series is connected to the negative side of the high voltage power source.

9. The spark-gap cutting blade of claim 1 wherein the central electrode in connected to the negative side of a high voltage power source and the last electrically conductive element in the series is connected to the positive side of the high voltage power source.

10. The spark-gap cutting blade of claim 1 wherein the cutting blade is circular, in cross section.

11. The spark-gap cutting blade of claim 1 wherein the cutting blade is elliptical in cross section.

12. The spark-gap cutting blade of claim 1 wherein the cutting blade is convex in cross section.

13. The spark-gap cutting blade of claim 1 wherein the cutting blade is concave in cross section.

* * * * *